United States Patent
Gillman et al.

(10) Patent No.: US 10,376,384 B2
(45) Date of Patent: Aug. 13, 2019

(54) DEVICES AND METHODS FOR HIP REPLACEMENT

(71) Applicant: Bullseye Hip Replacement, LLC, Las Vegas, NV (US)

(72) Inventors: Michael Gillman, Laguna Beach, CA (US); Benjamin A. Gillman, Laguna Beach, CA (US)

(73) Assignee: Bullseye Hip Replacement, LLC, Las Vegas, NV (US)

( * ) Notice: Subject to any disclaimer, the term of this patent is extended or adjusted under 35 U.S.C. 154(b) by 24 days.

(21) Appl. No.: 15/208,323

(22) Filed: Jul. 12, 2016

(65) Prior Publication Data
US 2017/0095353 A1 Apr. 6, 2017

Related U.S. Application Data

(63) Continuation of application No. 14/485,074, filed on Sep. 12, 2014, now Pat. No. 9,414,938.

(51) Int. Cl.
*A61F 2/30* (2006.01)
*A61F 2/34* (2006.01)
(Continued)

(52) U.S. Cl.
CPC ............ *A61F 2/4609* (2013.01); *A61B 34/10* (2016.02); *A61F 2/34* (2013.01); *A61F 2/46* (2013.01);
(Continued)

(58) Field of Classification Search
CPC .............. A61B 2017/568; A61B 34/10; A61B 2034/108; A61F 2/34; A61F 2/46
See application file for complete search history.

(56) References Cited

U.S. PATENT DOCUMENTS

| | | | |
|---|---|---|---|
| 5,474,560 A | 12/1995 | Rohr, Jr. | |
| 5,527,317 A | 6/1996 | Ashby et al. | |

(Continued)

FOREIGN PATENT DOCUMENTS

| | | |
|---|---|---|
| EP | 2168507 A2 | 3/2010 |
| WO | WO-2009098491 A1 | 8/2009 |

(Continued)

OTHER PUBLICATIONS

Biomet Orthopedics "Active Articulation™ Dual Mobility Hip System—Surgical Technique" 2011, 28 pages.
(Continued)

*Primary Examiner* — David W Bates
(74) *Attorney, Agent, or Firm* — Wilson Sonsini Goodrich & Rosati

(57) ABSTRACT

A device for use in placing a prosthesis in a patient during joint replacement surgery is disclosed. The device may comprise a body formed using medical imaging data corresponding to an anatomic structure of the patient and a final installation position of the prosthesis. The body may extend between a lower surface and an upper surface and may have an aperture extending therethrough. The body may also have an anatomic alignment member extending outward from an outer surface of the body and include an inner surface opposite the outer surface. The inner surface may define at least part of the aperture. The prosthesis alignment member may extend from the inner surface and the prosthesis alignment member may include a prosthesis alignment surface configured to align with a prosthesis in the final installation position.

9 Claims, 10 Drawing Sheets

(51) Int. Cl.
*A61F 2/46* (2006.01)
*A61B 34/10* (2016.01)

(52) U.S. Cl.
CPC ... *A61B 2034/105* (2016.02); *A61B 2034/108* (2016.02); *A61F 2/30942* (2013.01); *A61F 2002/30617* (2013.01); *A61F 2002/4662* (2013.01); *A61F 2002/4687* (2013.01)

(56) References Cited

U.S. PATENT DOCUMENTS

| | | | |
|---|---|---|---|
| 5,913,860 | A | 6/1999 | Scholl |
| 6,416,553 | B1 | 7/2002 | White et al. |
| 8,617,170 | B2 | 12/2013 | Ashby et al. |
| 8,617,171 | B2 | 12/2013 | Park et al. |
| 8,777,875 | B2 | 7/2014 | Park |
| 8,808,302 | B2 | 8/2014 | Roose et al. |
| 8,828,089 | B1 | 9/2014 | Perez et al. |
| 8,986,309 | B1 * | 3/2015 | Murphy ............. A61B 17/1746 606/87 |
| 8,998,909 | B2 | 4/2015 | Gillman et al. |
| 9,138,258 | B2 | 9/2015 | Geebelen |
| 9,204,977 | B2 | 12/2015 | Bollinger |
| 9,211,128 | B2 | 12/2015 | Gillman et al. |
| 9,414,938 | B2 | 8/2016 | Gillman et al. |
| 2003/0130741 | A1 | 7/2003 | McMinn |
| 2005/0148843 | A1 | 7/2005 | Roose et al. |
| 2007/0219562 | A1 | 9/2007 | Slone et al. |
| 2009/0163922 | A1 | 6/2009 | Meridew et al. |
| 2010/0016860 | A1 | 1/2010 | McCardel |
| 2010/0082035 | A1 | 4/2010 | Keefer |
| 2010/0274253 | A1 * | 10/2010 | Ure .................... A61B 17/1746 606/91 |
| 2011/0060342 | A1 * | 3/2011 | Turner ................. A61F 2/4609 606/91 |
| 2011/0093086 | A1 | 4/2011 | Witt et al. |
| 2011/0190775 | A1 | 8/2011 | Ure |
| 2011/0214279 | A1 | 9/2011 | Park et al. |
| 2011/0313424 | A1 * | 12/2011 | Bono ................. A61B 17/1746 606/91 |
| 2012/0041445 | A1 * | 2/2012 | Roose ................ A61B 17/1746 606/96 |
| 2012/0289965 | A1 * | 11/2012 | Gelaude ................ A61B 17/15 606/87 |
| 2012/0296339 | A1 | 11/2012 | Iannotti et al. |
| 2012/0303035 | A1 | 11/2012 | Geebelen |
| 2013/0123789 | A1 | 5/2013 | Park |
| 2013/0184764 | A1 | 7/2013 | Stone et al. |
| 2013/0190768 | A1 | 7/2013 | Aram et al. |
| 2013/0317510 | A1 | 11/2013 | Couture et al. |
| 2014/0025348 | A1 | 1/2014 | Abiven |
| 2014/0100579 | A1 | 4/2014 | Kelman et al. |
| 2014/0128875 | A1 | 5/2014 | Park et al. |
| 2014/0128876 | A1 | 5/2014 | Aram et al. |
| 2014/0135940 | A1 * | 5/2014 | Goldstein ............. A61B 17/15 623/22.21 |
| 2014/0142580 | A1 | 5/2014 | Aram et al. |
| 2014/0180296 | A1 | 6/2014 | Gillman et al. |
| 2014/0180430 | A1 | 6/2014 | Gillman et al. |
| 2014/0324181 | A1 | 10/2014 | Bergin et al. |
| 2014/0336660 | A1 * | 11/2014 | Gibson ................ A61F 2/4609 606/91 |
| 2015/0297248 | A1 * | 10/2015 | Gillman .................. A61F 2/34 606/87 |
| 2015/0305891 | A1 | 10/2015 | Bergin et al. |
| 2016/0250040 | A1 * | 9/2016 | Hermle ............. A61B 17/1746 606/91 |

FOREIGN PATENT DOCUMENTS

| | | |
|---|---|---|
| WO | WO-2010124164 A1 | 10/2010 |
| WO | WO-2011060536 A1 | 5/2011 |
| WO | WO-2011110374 A1 | 9/2011 |
| WO | WO-2012021846 A2 | 2/2012 |
| WO | WO-2012021849 A2 | 2/2012 |
| WO | WO-2012151393 A2 | 11/2012 |
| WO | WO-2012154407 A2 | 11/2012 |
| WO | WO-2013188960 A1 | 12/2013 |
| WO | WO-2016040655 A1 | 3/2016 |

OTHER PUBLICATIONS

Notice of Allowance dated May 12, 2016 for U.S. Appl. No. 14/485,074.
Notice of Allowance dated May 26, 2016 for U.S. Appl. No. 14/485,074.
Office action dated Mar. 2, 2015 for U.S. Appl. No. 14/485,074.
Office action dated Jun. 15, 2015 for U.S. Appl. No. 14/485,074.
Office action dated Dec. 15, 2015 for U.S. Appl. No. 14/485,074.
PCT/US2015/049457 International Preliminary Report on Patentability with Written Opinion dated Mar. 14, 2017.
PCT/US2015/049457 International Search Report dated Jan. 25, 2016.

* cited by examiner

DEVICES AND METHODS FOR HIP REPLACEMENT

CROSS-REFERENCE

This application is a continuation of U.S. application Ser. No. 14/485,074, filed Sep. 12, 2014, now U.S. Pat. No. 9,414,938, issued Aug. 16, 2016, which is incorporated herein by reference in its entirety and to which application we claim priority under 35 USC § 120.

BACKGROUND

Technical Field

The present disclosure relates to devices and methods for the replacement of joints, and more particularly, to patient-specific hip replacement devices, including methods of manufacturing and using such devices for achieving accurate placement of prosthetics based on computer generated imaging of a patient.

Description of the Related Art

One method of treating hip and other joints with arthritis and other medical conditions is to replace surfaces of articulating joints with prosthetic devices through surgical procedures. It is critical that such prosthetic devices are accurately designed and manufactured, and are installed correctly in order to relieve pain and provide an effective treatment method for such ailments. An orthopedic surgeon performing such joint replacement on a patient seeks to ensure, through surgery, adequate placement of the prosthetic and proper reconstruction of the joint being replaced. A particular patient's bone structure symmetry and kinematics are things a surgeon considers when performing joint replacement surgery. Malposition of joint replacement prosthetics can result in premature wear of the bearing surfaces, which may require additional surgeries to correct.

In the case of a hip, the condition of the patient's joint may require a partial or total replacement. A partial hip replacement involves replacing the femoral head (the ball) of the damaged hip joint; however, the acetabulum (the hip socket) is not replaced in a partial hip replacement surgery. A total hip replacement includes replacing both the femoral head and the acetabulum with prosthetic devices. The femoral head is replaced with a femoral prosthetic that typically includes a head portion and a stem. The stem extends into the femur of the patient and is utilized to secure the femoral device to the femur, with the head portion protruding out from the femur. In total hip replacement, the acetabulum is resurfaced and replaced with a cup-shaped acetabular device or prosthetic. The cup-shaped acetabular device provides a bearing surface for the head portion of the femoral prosthetic to allow a desirable amount of range of motion via the joint upon total hip replacement.

To replace the acetabulum effectively, a surgeon will typically enlarge the acetabulum with a reamer machine and reamer head to create a resurfaced cavity to receive a prosthetic acetabular cup, which may or may not be secured by cement or bone screws. One concern during the reaming portion of the surgery is that the cutting portion of the reamer is hemispherical while the prosthetic acetabular cup is typically sub-hemispherical. If the acetabulum is reamed too deeply, the prosthetic acetabular cup will be positioned too deep within the reamed cavity. If the acetabulum is reamed too shallowly, the prosthetic acetabular cup will not be positioned deep enough. If the acetabulum is reamed at an improper angle, the prosthetic acetabular cup will not be installed properly. These imperfections can cause malalignment of the prosthetic hip joint. Moreover even if the acetabular bone is properly reamed, it is quite difficult to place the acetabular prosthetic cup when using standard techniques. Recent studies reflect a 50% rate of error in placement of the acetabular cup from an acceptably optimal range of positions when standard techniques are utilized. Thus, accurate reaming of the acetabulum and accurate positioning of the prosthetic acetabular cup are critical.

With the assistance of computer generated data derived from CT, MRI, or other scans, such as X-rays, surgeons can more effectively determine proper alignment and positioning of the prosthetic acetabular cup in a patient through 3-D modeling and rendering. Some surgeons use lasers or peripheral guide pins during surgery in an attempt to properly place the prosthetic acetabular cup; however, accuracy and simplicity of existing devices and methods remain limited due to a variety of factors.

BRIEF SUMMARY

A device for use in placing a prosthesis in a patient during joint replacement surgery is disclosed. The device may comprise a first component formed using medical imaging data corresponding to an anatomic structure of the patient and a final installation position of the prosthesis and a second component formed using medical imaging data corresponding to the anatomic structure of the patient and the final installation position of the prosthesis. The first component may have a first body extending between a lower surface and an upper surface and an aperture extending therethrough. The first component may also have an anatomic alignment member extending outward from an outer surface of the first body. The anatomic alignment member may have a first alignment surface shaped to conform to an anatomic structure of the patient. The aperture may be at least partially defined by an inner surface extending between the upper surface and lower surface and the inner surface may be sized and shaped to receive the second component. The second component may include a an upper portion and a lower portion. The upper portion may be joined to the lower portion at an alignment rim sized and shaped to mate with a rim of the prosthesis and the lower portion may have a surface sized and shaped to conform to at least part of an internal surface of a prosthesis.

Another device for use in placing a prosthesis in a patient during joint replacement surgery is also disclosed. The device may comprise a body formed using medical imaging data corresponding to an anatomic structure of the patient and a final installation position of the prosthesis. The body may extend between a lower surface and an upper surface and may have an aperture extending therethrough. The body may also have an anatomic alignment member extending outward from an outer surface of the body and include an inner surface opposite the outer surface. The inner surface may define at least part of the aperture. The prosthesis alignment member may extend from the inner surface and the prosthesis alignment member may include a prosthesis alignment surface configured to align with a prosthesis in the final installation position.

A method for replacing a joint of a patient may be disclosed. The method may include generating a bone surface image. A prosthesis image superimposed on the bone surface image in an installation position of the prosthesis may be generated. A patient specific jig image superimposed proximate the bone surface image and the implant image according to the installation position of the prosthesis may be generated. The patient specific jig image may include a body including a lower surface and an opposite upper surface and having an aperture extending between the upper surface and the lower surface. The body may include a prosthesis alignment member extending from the inner surface. The prosthesis alignment member may include a prosthesis alignment surface configured to align with the prosthesis image in the final installation position. The method may also include generating control data from the patient specific jig image.

DETAILED DESCRIPTION

Figure 1:
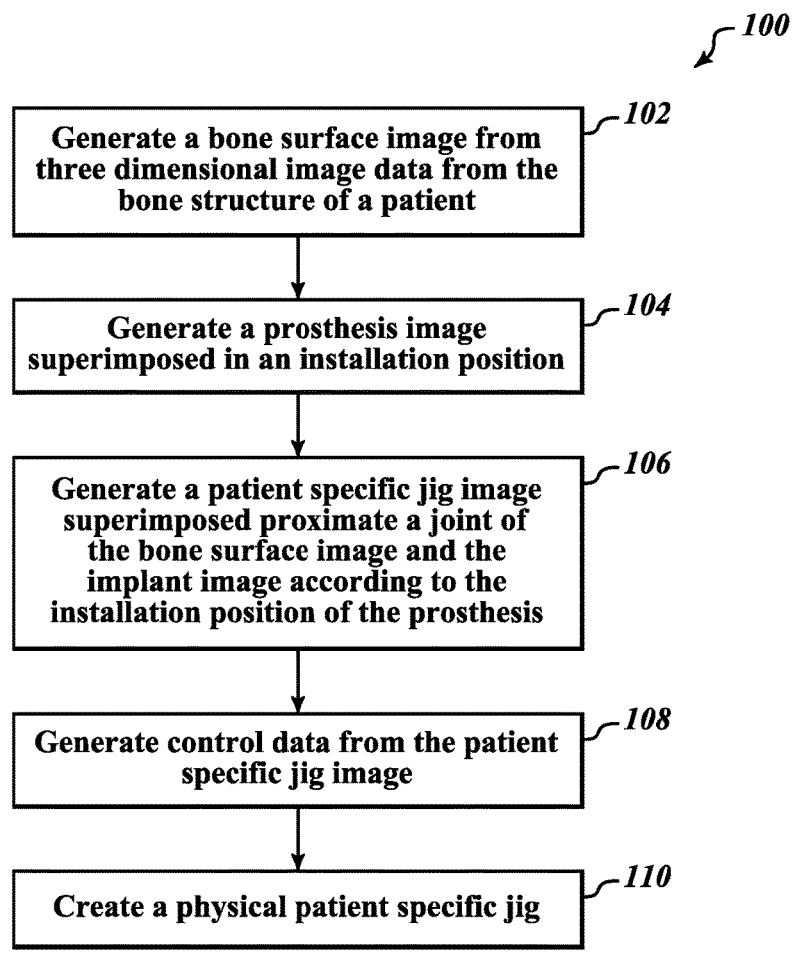
FIG. 1 depicts a method according to one or more embodiments disclosed herein.

The present disclosure pertains to patient-specific hip replacement devices and methods for designing and manufacturing such devices for achieving accurate acetabular component placement during hip replacement surgery based on computer generated imaging of a particular patient. When an orthopedic surgeon recommends total hip replacement surgery for a particular patient, a variety of images may be obtained utilizing CT, MRI, and other scans, such as x-rays, to generate 3-D modeling of the patient's bone structure, particularly the femur, the pelvic bone, and the coxal (hip) bone. From such 3-D models, the surgeon may determine the specific, final location and orientation of an acetabular cup to be secured to the patient's acetabulum during surgery. Once the final location and orientation of the acetabular cup is determined, the surgeon may create a patient-specific jig to be installed on the patient's acetabulum during the surgery to achieve or confirm accurate positioning of the prosthetics installed in the patient.

The patient-specific jig may be designed and manufactured based on a patient-specific acetabulum. The patient-specific jig can be developed as either physical components via a prototyping machine or visual representations in a 3-D modeling software program based upon the 3-D images of the patient.

The methods and systems disclosed herein are based at least in part on pre-operating (preoperative) imaging and at least in part on orthopedic surgical procedures based upon the preoperative methods and systems. As is understood in the art, preoperative imaging has a number of different purposes and generally is performed to help guide the surgeon during the surgical procedure, to allow for patient-specific tools or implants to be formed, etc. The present disclosure may be part of a system for designing and constructing one or more patient-specific jigs for use in an orthopedic surgical procedure in which an acetabular component is prepared, oriented, and implanted. The referenced systems and methods are now described with reference to the accompanying drawings, in which one or more illustrated embodiments or arrangements of the systems and methods are shown in accordance with one or more embodiments disclosed herein. Aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice, and is left to the implementer. Throughout this disclosure, the term "prosthetic implant" and "acetabular component" refer to cup-shaped implants that are installed into patients during hip replacement surgery.

Figure 2:
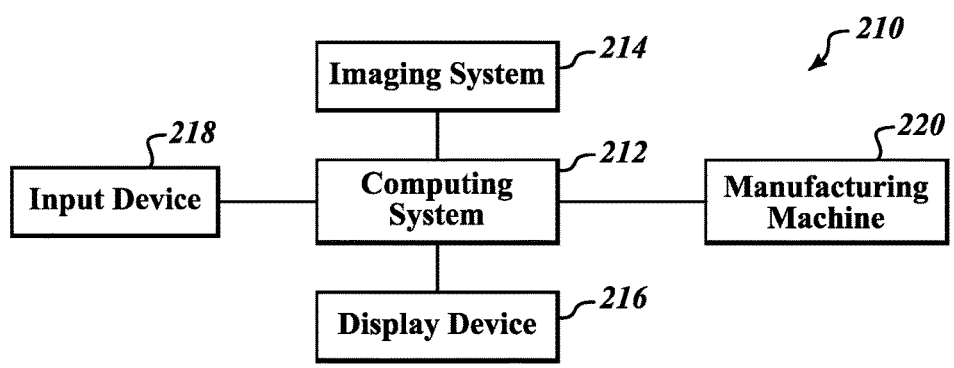
FIG. 2 depicts a system according to one or more embodiments disclosed herein.

FIG. 1 is a flow diagram illustrating a method pertaining to preoperative imaging and planning according to aspects of the present disclosure. FIG. 2 shows a system for carrying out the methods of the present disclosure, such as that described with reference to FIG. 1. FIG. 2 shows a simplified system 210 of devices that may be used to carry out the methods of the present disclosure. The system 210 comprises a computing system 212 coupled to an imaging system 214. The imaging system 214 captures patient image data and transfers the data to the computing system 212. The computing system 212 processes such data and transmits the data to a display device 216 for display of images and other data. An input device 218 receives input from a computer or an operator (such as a surgeon) and transmits inputted information to the computing system 212 for processing. Such input devices 218 are well known in the art and will not be described in greater detail. The imaging system 214 may include a bone imaging machine for forming three-dimensional image data from a bone structure of a patient. The computing system 212 may include a patient-specific device generator for processing and generating images, and a patient-specific device converter for generating design control data. A manufacturing machine 220 receives the control data from the computing system 212 for making patient-specific jigs.

In FIG. 1, a method 100 according to an embodiment may start at block 102. At block 102, a bone imaging machine generates a bone surface image from three-dimensional image data from the bone structure of a patient. At block 104, a patient-specific device generator generates a prosthesis image superimposed on an acetabulum of the bone surface image. The prosthesis image is positioned in its final, implanted position and orientation, regardless of the state of the patient's bone in the bone surface image. An outer surface of the prosthesis image may determine the surface of the reamed acetabulum of the patient. For example, by placing the prosthesis image in the final, implanted position and orientation, a doctor may determine the final shape and orientation of the reamed acetabulum such that a prosthesis may be inserted or implanted into the patient's reamed acetabulum in the correct final, implanted position and orientation. The jigs created from the present disclosure may be designed to install or confirm proper installment of a prosthesis during a hip replacement procedure.

At block 106, the patient-specific device generator generates a patient specific jig image superimposed proximate the acetabulum of the bone surface image and the prosthesis image according to the installation position. The patient-specific device generator may use the bone surface image to create a patient-specific device with anatomic engagement members that have an engagement surface that corresponds to, matches, or is the negative contour of the patient's anatomy. The patient-specific device generator may use the prosthesis image to generate prosthesis engagement members that engage with features of the prosthesis, such as a surface or rim of the prosthesis. The patient-specific device generator may also use the prosthesis image and the bone surface image to generate jig alignment features or members.

At block 108, a patient-specific device converter generates control data from the patient-specific jig image. The control data may be used by a machine during a manufacturing process to create physical patient-specific jigs by additive or subtractive machining, such as fused deposition modeling, stereolithography, or other methods. At block 110, the manufacturing device creates a physical patient-specific jig.

As discussed above, FIG. 2 shows the system 210 for carrying out the methods of FIG. 1 according to some aspects of the present disclosure. The computing system 212 may include instructions in the form of computer software for automatically generating images of prosthesis implants in final installation positions on the bone structure images. In some aspects, it may be necessary for the surgeon during preoperative planning to input information into the input device 218 for creating or altering jig images or prostheses images for a particular patient based on the surgeon's understanding of the particular bone structure of the patient as displayed on the display device 216.

Figure 3:
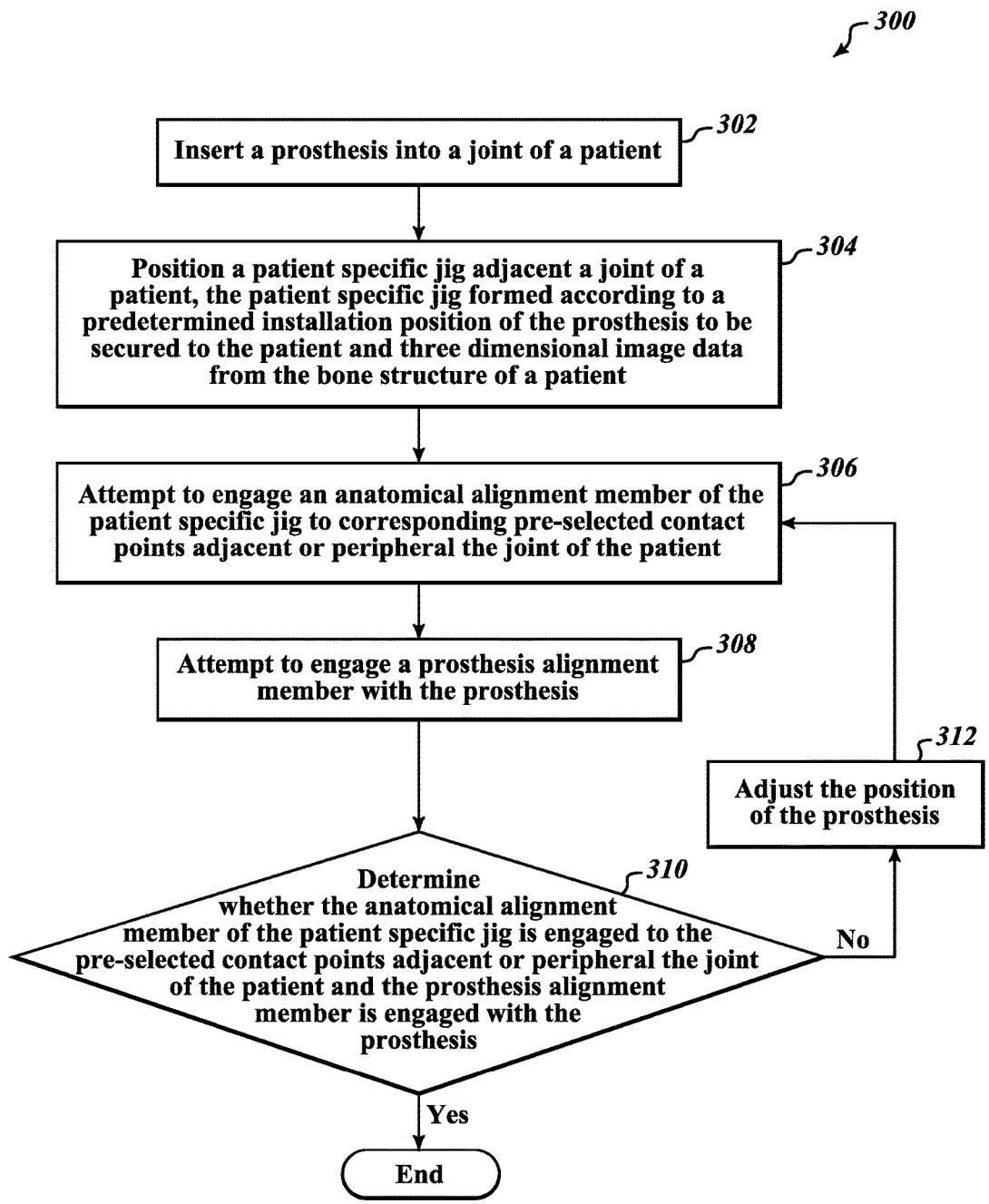
FIG. 3 depicts a method according to one or more embodiments disclosed herein.
Figure 4:
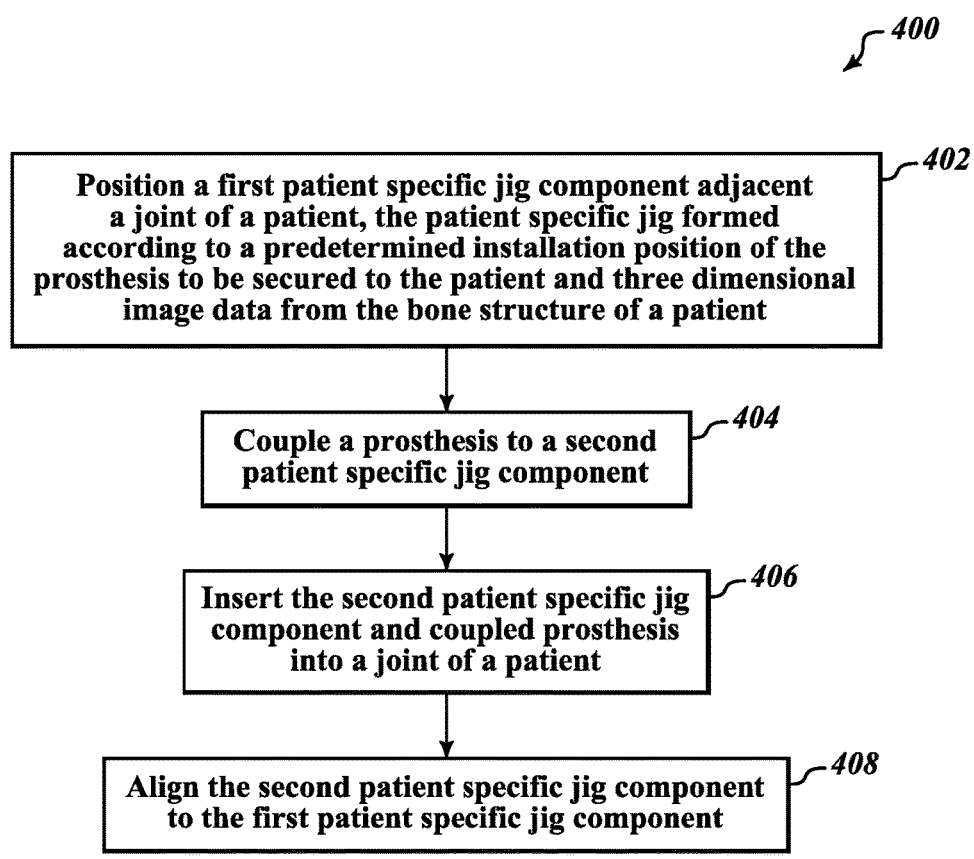
FIG. 4 depicts a method according to one or more embodiments disclosed herein.

FIGS. 3 and 4 are flow diagrams of methods pertaining to operative surgery according to aspects of the present disclosure. The methods of FIGS. 3 and 4 may be carried out by a surgeon or by a machine, or by both. Moreover, the process may utilize some or all of the devices discussed with reference to FIGS. 1 and 2 during surgery, such as viewing the preoperative images displayed on the display device while operating on a patient.

In FIG. 3, a method 300 according to an embodiment disclosed herein may start at block 302. The method 300 may be carried out using a patient specific jig, such as, for example, shown in FIGS. 9-13. In hip replacement procedures, almost all patients have their acetabulum reshaped to accept a prosthetic acetabulum. The acetabulum may be reamed or otherwise reshaped to accept the prosthesis in any manner. Once a doctor or machine shapes the acetabulum to the correct shape, at block 302, the prosthesis is inserted into a reamed acetabulum of a patient. A doctor may insert the prosthesis by hand, using an impactor tool, or using another tool to insert the prosthesis. A reamed acetabulum may be reamed to have a radius or shape that is slightly smaller than the radius or shape of the acetabular component. As such, the surgeon typically utilizes a mallet or other tool to impact the prosthesis into its final position. In some embodiments, the doctor may place the prosthesis into the reamed acetabulum in a position and orientation approximate the final implantation position and then use an impactor tool to place the prosthesis in its final position.

At block 304, a doctor or machine may place a patient specific jig adjacent an acetabulum of a patient, the patient specific jig formed according to a predetermined installation position of the prosthesis to be secured to the patient and three-dimensional image data from the bone structure of a patient. Placing the patient specific jig may include aligning an anatomical alignment member of the patient specific jig to corresponding pre-selected areas adjacent or peripheral the acetabulum of the patient and also aligning a prosthesis alignment member with the prosthesis. For example, after placing the prosthesis into the reamed acetabulum by hand, a doctor may position the patient specific jig and align, but possibly not engage, the various alignment members of the patient specific jig with anatomical features adjacent an acetabulum of a patient and the prosthesis. By positioning the jig in such a manner, the doctor may evaluate the initial position of the prosthesis and may make adjustments to the initial position of the prosthesis before attempting to place the prosthesis in its final or predetermined installation position.

At block 306, a doctor or machine may attempt to engage an anatomical alignment member of the patient specific jig corresponding to pre-selected areas adjacent to or on the periphery of the acetabulum of the patient. And at block 308, a doctor or machine may attempt to engage a prosthesis alignment member with the prosthesis.

If the acetabular prosthesis has been placed in the correct final installation position, the anatomical alignment member of the patient specific jig should engage with the corresponding to pre-selected areas adjacent or peripheral the acetabulum of the patient, and the prosthesis alignment member should engage with the acetabular prosthesis. Thus, at block 310, a doctor or machine may inspect the alignment and engagement of the alignment members and determine whether the anatomical alignment member of the patient specific jig is engaged to the pre-selected areas adjacent or peripheral the acetabulum of the patient, and the prosthesis alignment member is engaged with the prosthesis. If the alignment members are properly engaged, then the acetabular prosthesis is installed in the correct installation position and orientation. If the alignment members are not properly engaged, then the acetabular prosthesis is not in the correct final installation position.

Furthermore, an evaluation of the engagement members relative to the patient's anatomy or the acetabular prosthesis may help quantify displacement of the current position of the acetabular prosthesis with the final installation position of the acetabular prosthesis. For example, by looking at the alignment members and their positions relative to the prosthesis and the patient's anatomy, a doctor may determine how far the prosthesis should be rotated or how much deeper the prosthesis should be driven into the patient's acetabulum in order to place the prosthesis in the final installation position.

At block 312, a doctor or machine may adjust the position of the acetabular prosthesis. Once the adjustment is complete, the process may return to block 306. In some embodiments, the process may return to block 304 or block 308. In addition, in some embodiments, depending, for example, on the steps a doctor or machine uses to adjust the position and orientation of the prosthesis at block 312, one or more of blocks 304, 306, or 308 may be omitted. In some embodiments, the position and orientation of the prosthesis may be such that the prosthesis should be removed and the process may begin again at block 302.

In FIG. 4, a method 400 according to an embodiment disclosed herein may start at block 402. The method 400 may be carried out using a patient specific jig, such as, for example, shown in FIGS. 7 and 8. At block 402, a doctor may position a first patient specific jig component adjacent an acetabulum of a patient. The patient specific jig may be formed according to a predetermined installation position of the prosthesis to be secured to the patient and three-dimensional image data from the bone structure of a patient. Positioning the first patient specific jig component may also include engaging an anatomic alignment member with the anatomic structure adjacent the acetabulum of the patient.

At block 404, a doctor or machine may couple a prosthesis to a second patient specific jig component. In some embodiments, for example, as shown in the embodiment depicted in FIGS. 7 and 8, a surface of the second patient specific jig component may match an inner surface of the acetabular prosthesis such that, by pressing the acetabular prosthesis onto the second patient specific jig component, the jig component holds the prosthesis.

At block 406, the second patient specific jig component and the prosthesis are inserted into the patient's reamed acetabulum. In some embodiments, the second patient specific jig component and the prosthesis are inserted while coupled together, for example, in embodiments where the prosthesis is coupled to the second patient specific jig before being inserted into the acetabulum. In some embodiments, the acetabular prosthesis may be inserted into the reamed acetabulum before the second patient specific jig component is inserted.

At block 408, the second patient specific jig component is aligned with the first patient specific jig component. The alignment of the two jigs indicates that the acetabular prosthesis is installed in the correct final installation position, as determined during the preoperative analysis. In some embodiments, a doctor may align the two jig components by using an impactor tool to drive the acetabular prosthesis into the reamed acetabulum and into the final installation position. As described elsewhere in this disclosure, the first and second patient specific jig components may be aligned in a number of different ways. In some embodiments, alignment keys may be used to align and verify correct alignment of the jigs; in some embodiments, a surface of the first jig component may align with the surface of the second jig component. In some embodiments, a mark, surface indicator, or other indicator may be used on one or both of the first and second jig components to aid in alignment.

Figure 5:
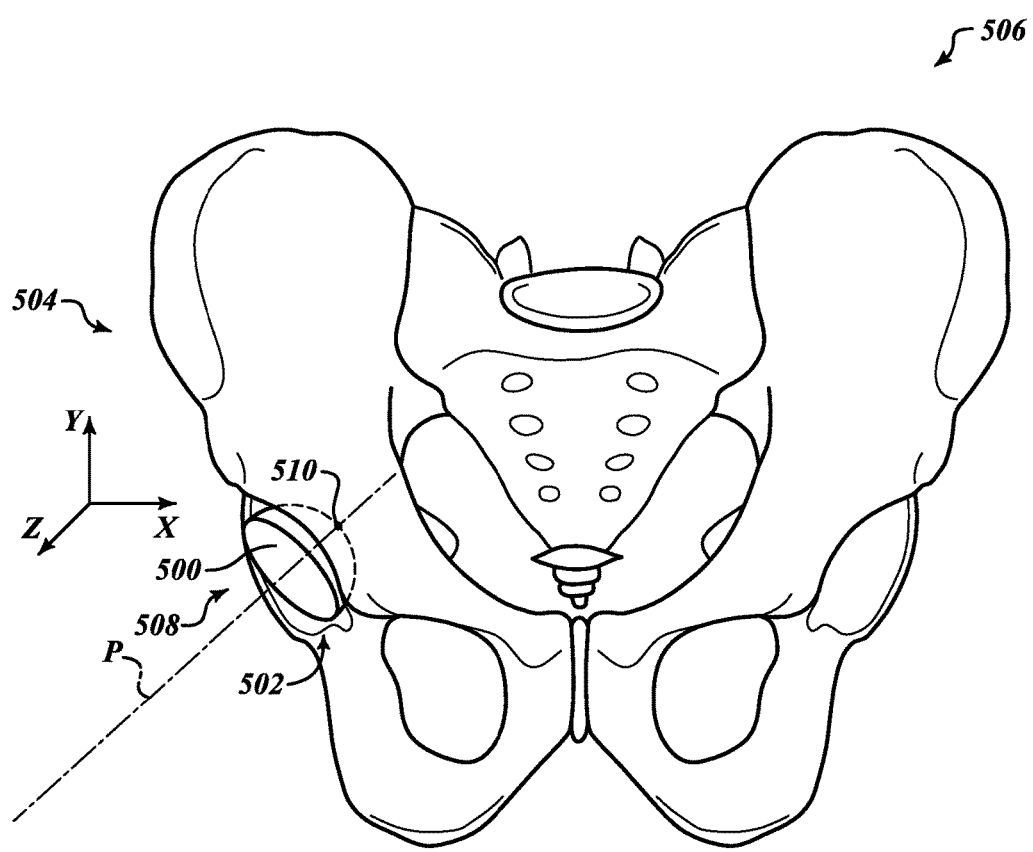
FIG. 5 depicts a front view of a pelvic bone with an installed acetabular prosthesis according to one or more embodiments disclosed herein.
Figure 6:
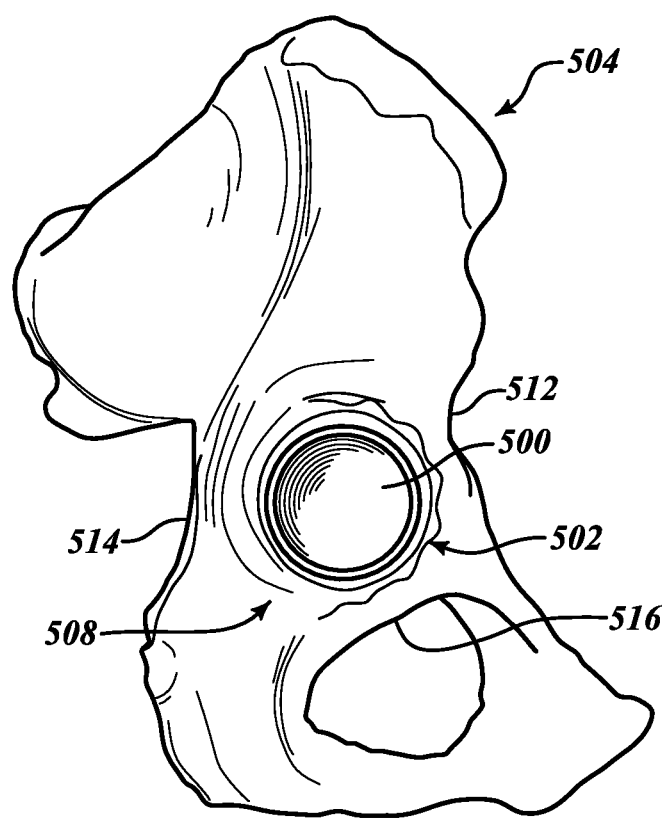
FIG. 6 depicts a top view of a pelvic bone of FIG. 5 with an installed acetabular prosthesis according to one or more embodiments disclosed herein.

FIGS. 5 and 6 show an acetabular component 500 oriented in an acetabulum 502 of a coxal bone 504 of a pelvic bone 506. The acetabular component 500 is positioned according to an installation position 508, which is in part determined by a prescribed anteversion angle and a prescribed inclination angle of the acetabular component 500. FIG. 5 shows a front view of the pelvic bone 506 and the acetabular component 500 positioned in the acetabulum 502 of the patient's right coxal bone 504, and FIG. 6 shows a lateral view of the right coxal bone 504 with the acetabular component 500 positioned in the acetabulum 502. These figures illustrate the incorporation of the methods and devices discussed herein where the acetabular component 500 may be a generated image that is superimposed over a generated image of bone structure or patient anatomy (e.g., the coxal bone 504) of a patient to determine an installation position 508 of the acetabular component 500. FIGS. 5 and 6 may also represent a physical acetabular component or prosthesis installed in a final installation position in a patient's actual coxal bone.

Determining the prescribed anteversion angle and the prescribed inclination angle for a particular patient involves techniques and calculations that are known in the art, and thus, will not be described in detail. Although not necessarily part of the preoperative planning, for purposes of illustration an installation axis P is shown on FIG. 5.

Once the installation position 508 is determined, a reference point 510 is established that represents a particular point in the coxal bone 504 of the patient for purposes of determining the depth to which a reaming machine will ream bone material. The reference point 510 may be considered a point on the tangential plane of a hemispherical shaped surface, such as the outer surface shape of the acetabular component 500.

With continued reference to FIGS. 5 and 6, the coxal bone 504 includes, among other anatomical features, a medial rim 512, a sciatic notch 514, and an obturator foramen 516, which all have various shapes and surfaces that are specific to each patient. The anatomical features including the medial rim 512, the sciatic notch 514, and the obturator foramen 516 are potential anatomic reference features to which alignment members of a patient specific jig may align or engage.

Figure 7:
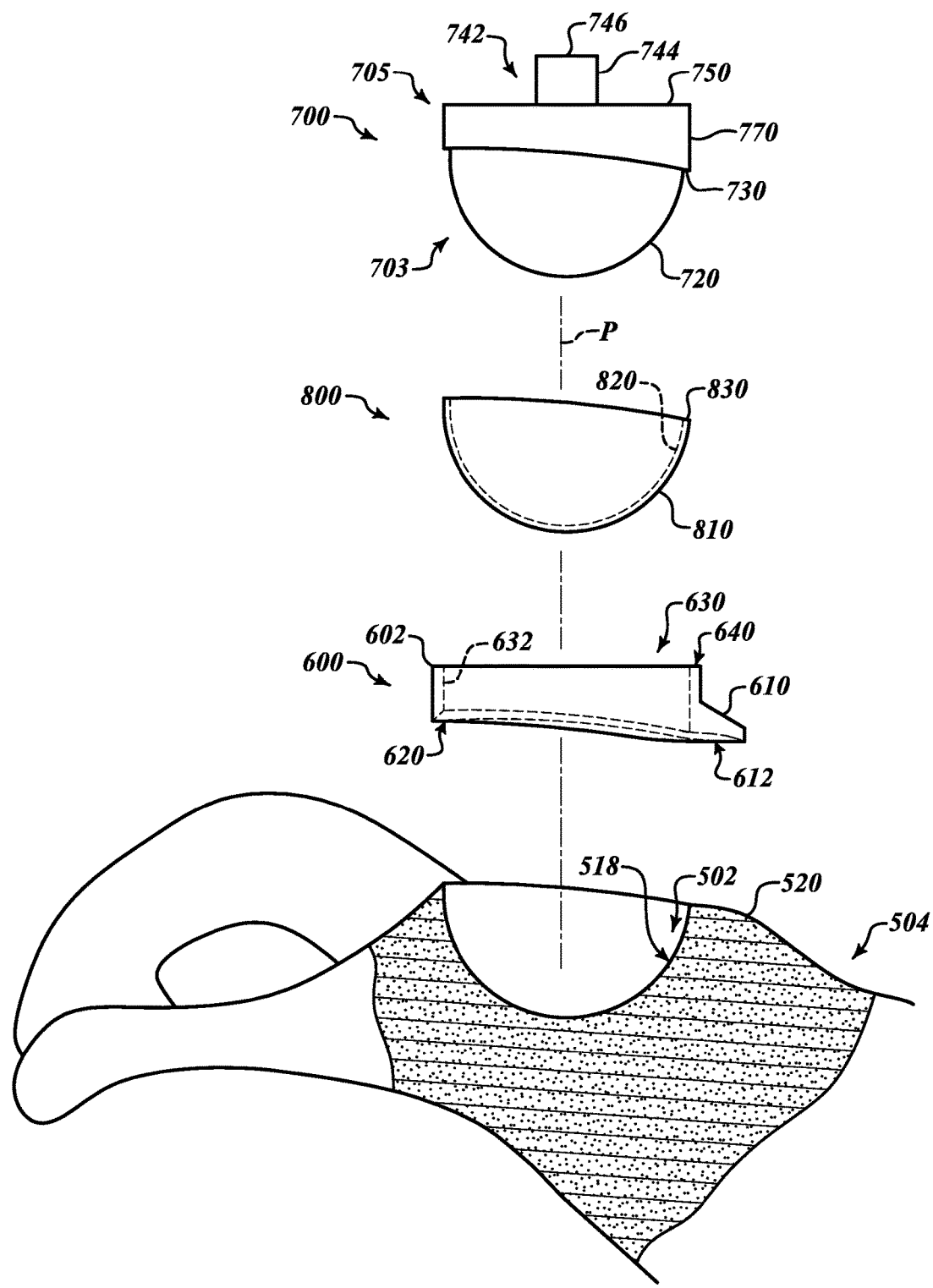
FIG. 7 depicts an exploded view of a device for hip replacement according to one or more embodiments disclosed herein.
Figure 8:
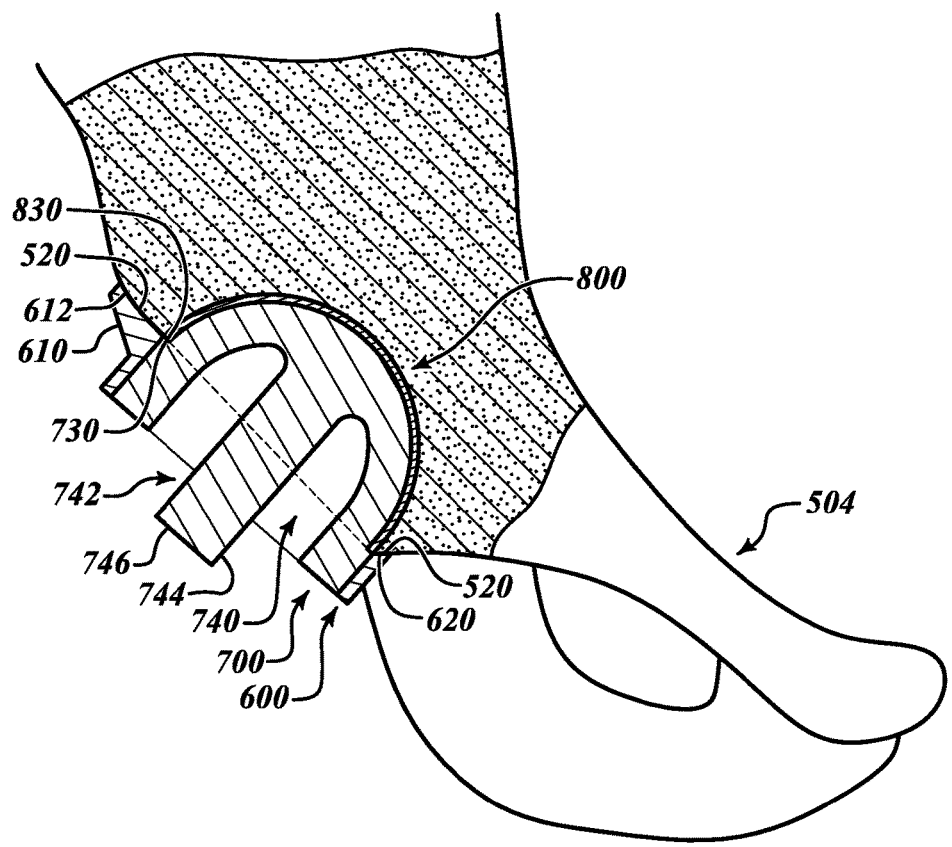
FIG. 8 depicts a cross-sectional view of a device for hip replacement according to one or more embodiments disclosed herein.

FIGS. 7 and 8 depict a device for hip replacement, a prosthesis, and a cross section of a coxal bone. FIG. 7 shows an exploded view of the device and prosthesis while FIG. 8 shows a cross section of the device and prosthesis in a final installation position within a patient's reamed acetabulum. The device for hip replacement includes a first patient specific jig component 600 that aligns with or engages with the anatomic structure of a patient and a second patient specific jig component 700 that aligns with the first patient specific jig component 600 and a prosthesis 800 to place the prosthesis 800 into the reamed acetabulum 502 of the patient.

The prosthesis 800 is a replacement acetabulum that a doctor inserts into the reamed acetabulum of a patient in a full hip replacement operation. The prosthesis 800, or acetabular cup, includes an outer surface 810 that matches the reamed surface 518 of the acetabulum 502. In some embodiments, the outer surface 810 of the prosthesis 800 is larger than the reamed acetabulum such that the prosthesis 800 is forced, hammered, pressed, or otherwise press fit into the acetabulum of a patient and held in place by an outward force of the prosthesis 800 on the reamed acetabulum 502. The inner surface 820 defines the inside of the prosthesis 800. An inner surface 820 is shaped to accept a prosthetic femoral head, not shown. The prosthesis 800 may also include a rim 830. The rim 830 may function as a reference location used to determine whether the prosthesis 800 is at a final installation position.

The first patient specific jig component 600 includes a body 602 and a radially or outwardly extending alignment member 610. In some embodiments, the body 602 may be circular or annularly shaped with a central aperture 630. The body 602 includes an alignment surface 620. The alignment surface 620 may be shaped to match the rim of the acetabulum 502 such that the surface 620 and, therefore, the body 602 may align with the anatomic structure of a patient in one position or orientation. The alignment member 610 also includes an alignment surface 612 that conforms or matches the anatomic surface structure 520 of a patient. For example, one or more alignment members 610 may align or engage with a point or area of the medial rim 512, the sciatic notch 514, the obturator foramen 516, or other surfaces or contact points.

The aperture 630 of the body 602 is defined by a guide surface 632, also called an aperture wall. The guide surface 632 may be concentric around the installation axis P. The guide surface 632 matches a jig alignment surface 770 of the second component 700. In some embodiments, the guide surface 632 is sized and shaped to accept the second patient specific jig component 700. In some embodiments, the aperture 630 or the guide surface may be sized and shaped such that the second patient specific jig component 700 can be inserted into the aperture 630 in only a single orientation.

The second patient specific jig component 700 may include an upper portion 705 and a lower portion 703. The lower portion 703 may include a mating surface 720 that extends from the upper portion 705 and is sized and shaped to match the inner surface 820 of the prosthesis 800, and may have a hemispherical shape. In other embodiments, only a portion of the mating surface 720 is sized and shaped to match the inner surface of the prosthesis 800. The mating surface 720 may be inserted into the reamed acetabulum 502 of a patient during placement of the prosthesis.

The second component 700 also includes the upper portion 705, which extends from an upper end of mating surface 720. The upper portion 705 may include alignment features 750, 770. The upper portion 705 and the mating surface 720 intersect at a rim 730 that extends around some or all of the second component 700. The rim 730 is shaped to match at least a portion of the rim 830 of the prosthesis 800.

The rim 730 may help align and place the prosthesis 800 in a final installation position. An acetabular prosthesis such as the prosthesis 800 may have a hemispherical shape of a known diameter. Thus, by knowing the position and orientation of the rim 830, a doctor can know the position and orientation of the prosthesis 800 and, in particular, the position and orientation of its inner surface 820.

The upper portion 705 may also include the cylindrically shaped jig alignment surface 770. The jig alignment surface 770 is sized and shaped to slidingly engage with the guide surface 632 of the first portion of the patient specific jig component 600. The jig alignment surface 770 and guide surface 632 may engage such that they align the central axis of the prosthesis 800 with the installation axis P of the final installation position of the prosthesis.

The upper portion 705 may also include a depth alignment feature, for example, the alignment surface 750. The alignment surface 750 may align with an alignment surface 640 to indicate that the prosthesis 800 is at the correct depth according to the final installation position of the prosthesis. For example, as a doctor places the prosthesis 800 and the second component through the first patient specific jig component 600 and into the acetabulum 502, the doctor can monitor the relative position of the depth alignment surface 750 of the second component 700 with the alignment surface 640 of the first component. When the two alignment surfaces 750, 640 are coplanar, the doctor will know that the prosthesis 800 is at the correct depth according to the final installation position. In other embodiments, the alignment surfaces 750, 640 may be at different locations or, rather than being coplanar to indicate information, such as the depth of the prosthesis 800, to the doctor, the two alignment surfaces may contact each other to indicate information to the doctor.

As shown in FIG. 8, the second component 700 may include a hollow inner area or cavity 740. Using a cavity 740 may save weight as compared to a jig with a solid inner area.

The second component 700 may also include a member 742 that extends from the cavity 740. The member 742 may extend out from the cavity 740 and beyond the alignment surface 750. The member 742 may include a gripping surface 744 for the doctor to hold while inserting the second component 700 through the aperture 630 in the first patient specific jig component 600 and into the reamed acetabulum 502 of the patient. In some embodiments, the member 742 may include an impact surface, such as impact surface 746. A doctor may use a mallet or other impact device to install the prosthesis 800 by striking the impact surface 746 with the mallet or other impact device.

Figure 9:
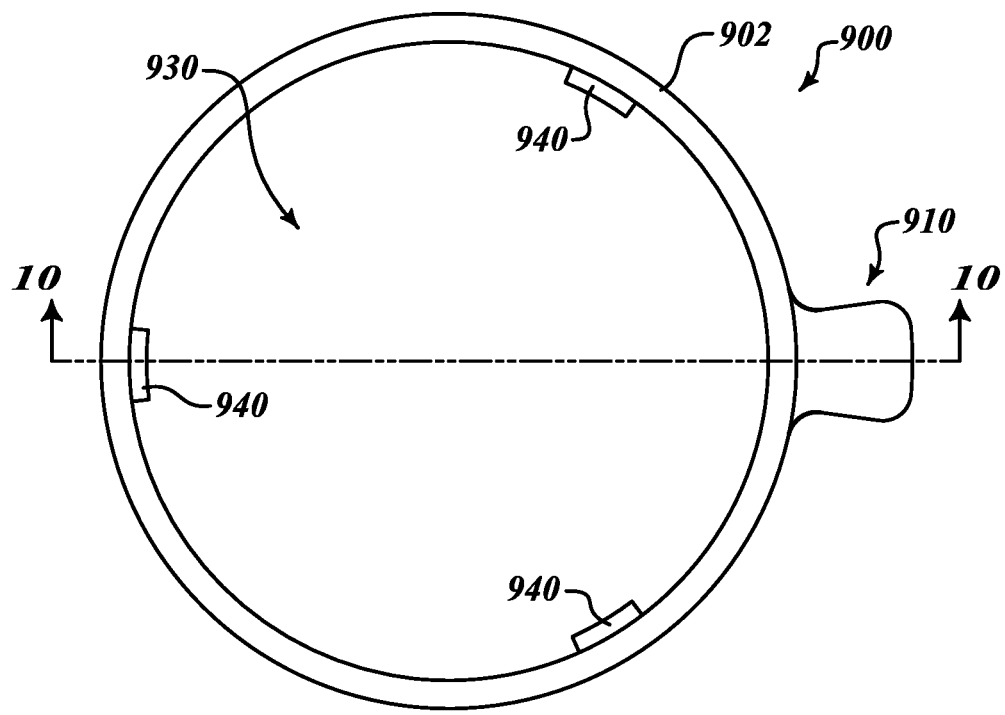
FIG. 9 depicts a top view of a device for hip replacement according to one or more embodiments disclosed herein.
Figure 10:
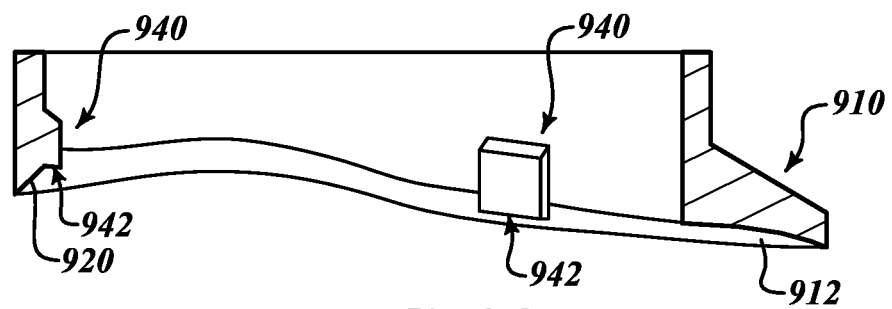
FIG. 10 depicts a cross-sectional view of the device for hip replacement of FIG. 9.
Figure 11:
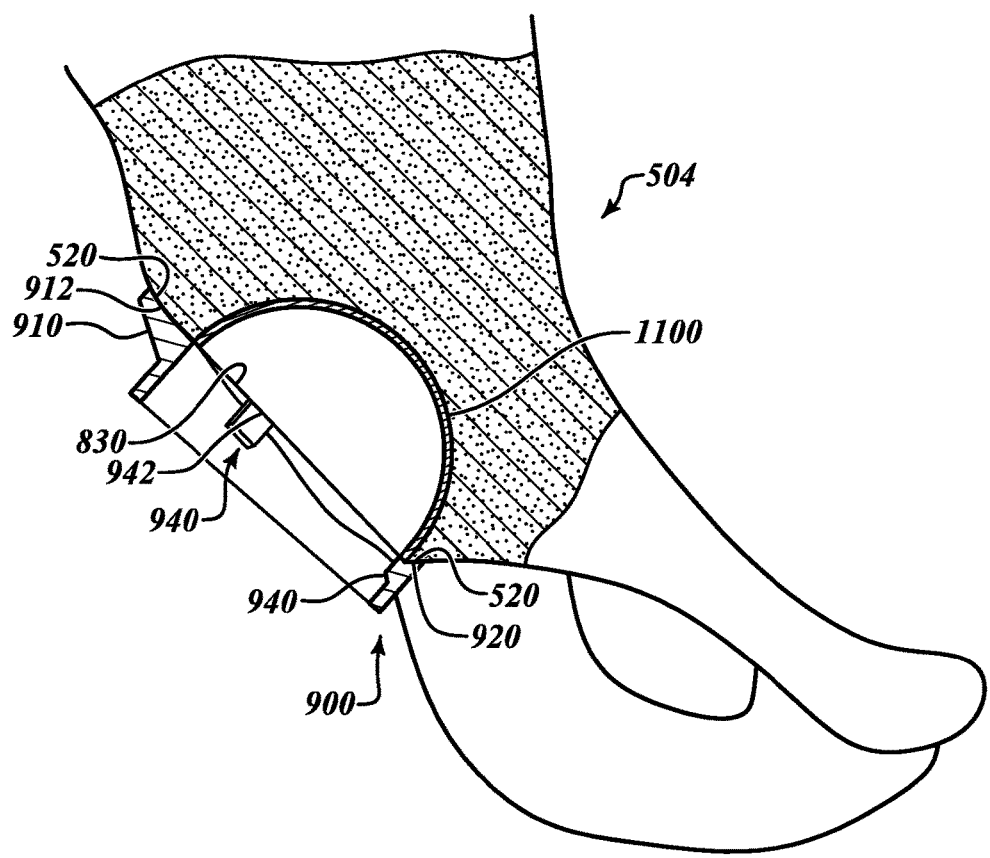
FIG. 11 depicts a cross-sectional view of the device of FIG. 9 installed according to one or more embodiments disclosed herein.

Referring now to FIGS. 9-11, an embodiment of a device for installing and verifying the installation position of a prosthesis is shown. The device is a patient specific jig 900. The patient specific jig 900 includes a body 902 and a radially extending anatomic alignment member 910 and may be circular or annularly shaped with a central aperture 930. The body 902 includes one or more anatomic alignment members 910 and one or more prosthesis alignment members 940. The anatomic alignment member 910 also includes an alignment surface 912 that conforms or matches the anatomic surface structure 520 of a patient. For example, one or more alignment members 910 may align or engage with a point or area on the medial rim 512, the sciatic notch 514, the obturator foramen 516, or other surfaces (see FIGS. 6 and 7). The alignment surface 912 may include a surface shape or contours that match the surface shape or contours of the anatomic structure with which the anatomic alignment member 910 aligns.

The shape and contours of the alignment surface 912 may be determined based upon the 3-D modeling images of the patient, a combination of two-dimensional radiographic images of the patient, or a combination of three-dimensional and two-dimensional images of a patient. The shape of the surface 912 is sometimes referred to as a negative of the anatomic structure with which the surface 912 aligns or engages. It is a negative because, for example, a protrusion on the anatomic surface structure 520 corresponds to a depression on the alignment surface 912 while a depression on the anatomic surface structure 520 corresponds to a protrusion on the alignment surface 912. Although depicted as having a single alignment member with a single alignment surface, in some embodiments, a patient specific jig may have more than one alignment member and alignment surface.

The body 902 includes an alignment surface 920. The shape and contours of the alignment surface 920 may be determined based upon the 3-D modeling images of the patient, a combination of two-dimensional radiographic images of the patient, or a combination of three-dimensional and two-dimensional images of a patient. The alignment surface 920 may be shaped to match the rim of the acetabulum 502 such that the surface 920 contacts the anatomic structure around the entire acetabulum. By aligning the alignment surface 920 with a point or area surrounding the acetabulum 502, the body 902 may align with the anatomic structure of a patient.

A patient specific jig may include one or more prosthesis alignment structures. For example, the patient specific jig 900 includes three prosthesis alignment members 940 that extend from the body 902. The prosthesis alignment members 940 include an alignment surface 942. The shape and contours of the alignment surface 942 may be determined based upon the 3-D modeling images of the patient, a combination of two-dimensional radiographic images of the patient, or a combination of three-dimensional and two-dimensional images of a patient. For example, a patient-specific device generator may generate a prosthesis image in its final implanted position and orientation and then generate a patient specific jig corresponding to the final implanted position. In such an embodiment, the anatomic alignment members 910 and their corresponding anatomic alignment surfaces 912 may be generated to align or engage with the anatomic structures of the patient near the acetabulum while the prosthesis alignment members 940 and their corresponding alignment surfaces 942 may be generated to align with the rim and a prosthetic acetabulum when in the final implanted position. In this way, a doctor may use a physical patient specific jig manufactured according to the final installation position of the prosthesis and the patient's specific anatomic structure.

A doctor may use a patient specific jig, such as the patient specific jig 900, during a hip replacement operation. For example, after reaming or otherwise preparing a patient's acetabulum, the doctor may insert the prosthetic acetabulum into to the patient's acetabulum and attempt to place it in a final installation position and orientation. After placing the prosthetic, a doctor may align or engage the patient specific jig, such as patient specific jig 900, with the anatomic structure of the patient and then observe the alignment or misalignment of the prosthetic alignment structures and prosthetic alignment surfaces with the rim or other portion of the prosthetic. The alignment or misalignment of the prosthetic alignment surfaces with the rim or other portion of the prosthetic indicate information to the doctor regarding the position of the prosthetic. For example, if the prosthetic alignment surfaces align with the rim of the prosthetic, then a doctor may know that the prosthetic is in its final installation position, while misaligned alignment surfaces and rim may indicate how the position of the prosthetic should be changed to move the prosthetic into the final installation position. For example, the misalignment of the surfaces may indicate that the prosthetic should be set further into the reamed acetabulum of the patient, or the misalignment may indicate that the prosthetic's central axis is not in the correct orientation and the prosthetic should be tilted to align the central axis with the installation axis.

FIG. 11 shows a cross section of a coxal bone 504 with an installed prosthetic 1100 and an engaged patient specific jig 900. In this embodiment, the anatomic alignment member 910 is engaged with a corresponding portion of the patient's anatomic surface structure 520, and the prosthetic alignment member 940 is engaged with the rim 830 of the prosthesis. This arrangement indicates that the prosthesis 800 is in a final installation position.

Figure 12:
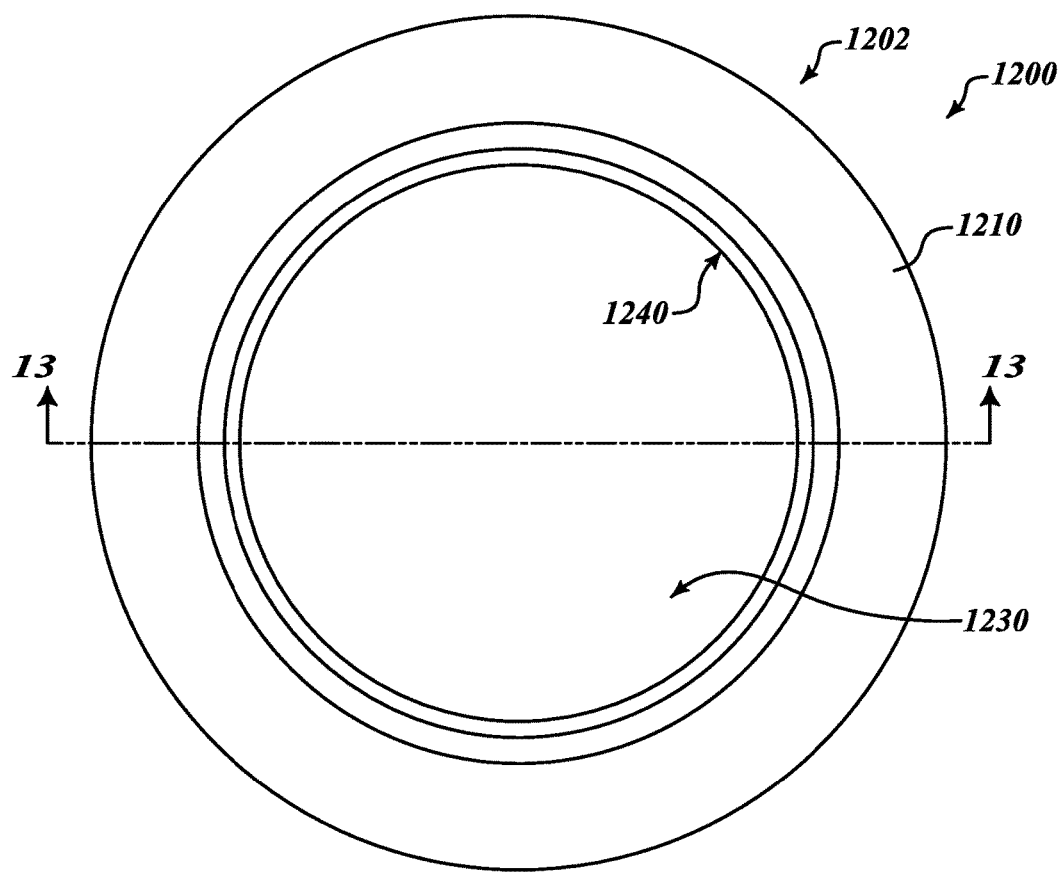
FIG. 12 depicts a top view of a device for hip replacement according to one or more embodiments disclosed herein.
Figure 13:
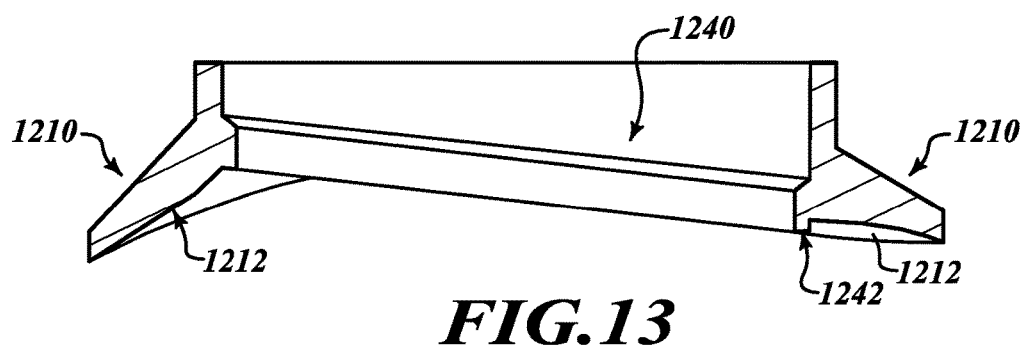
FIG. 13 depicts a cross-sectional view of the device for hip replacement of FIG. 12.

Referring now to FIGS. 12 and 13, an embodiment of a device for installing and verifying the installation position of a prosthesis is shown. The device is a patient specific jig 1200. The patient specific jig 1200 includes a body 1202 and a radially extending anatomic alignment member 1210 and may be circularly or annularly shaped with a central aperture 1230. The body 1202 includes one or more anatomic alignment members 1210 and one or more prosthesis alignment members 1240. The anatomic alignment member 1210 also includes an alignment surface 1212 that conforms or matches the anatomic surface structure of a patient. For example, the alignment member 1210 shown in FIGS. 12 and 13 extends around the entire circumference of the patient specific jig 1200 and therefore may align or engage with the anatomic structure of the patient in the area surrounding the patient's acetabulum. The alignment surface 1212 may include a surface shape or contours that match the surface shape or contours of the anatomic structure with which the anatomic alignment member 1210 aligns.

The shape and contours of the alignment surface 1212 may be determined based upon the 3-D modeling images of the patient, a combination of two-dimensional radiographic images of the patient, or a combination of three-dimensional and two-dimensional images of a patient.

The patient specific jig 1200 may include one or more prosthesis alignment members 1240. For example, the patient specific jig 1200 includes a single prosthesis alignment member 1240 that extends from the body 1202. The prosthesis alignment member 1240 includes an alignment surface 1242. The shape and contour of the alignment surface 1242 may be determined based upon the 3-D modeling images of the patient, a combination of two-dimensional radiographic images of the patient, or a combination of three-dimensional and two-dimensional images of a patient. For example, a patient-specific device generator may generate a prosthesis image in its final implanted position and orientation and then generate a patient specific jig corresponding to the final implanted position. In such an embodiment, the anatomic alignment member 1210 and the corresponding anatomic alignment surface 1212 may be generated to align or engage with the anatomic structures of the patient near the acetabulum while the prosthesis alignment member 1240 and the corresponding alignment surface 1242 may be generated to align with the rim and a prosthetic acetabulum when in the final implanted position. In this way, a doctor may use a physical patient specific jig manufactured according to the final installation position of the prosthesis and the patient's specific anatomic structure.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for use in placing a prosthesis in a patient during joint replacement surgery, the device comprising:
   a body having an annular shape;
   a first alignment member extending outward from an outer surface of the body, the first alignment member shaped to conform to an anatomic structure of the patient and mate with the anatomic structure in a single orientation;
   an inner surface defining an aperture through the body; and
   a prosthesis alignment member protruding radially inward from the inner surface of the body, into the aperture of the body, the prosthesis alignment member having a surface shaped to align with a prosthesis in an installation position on the patient during the joint replacement surgery, the surface shape of the prosthesis alignment member based on a three-dimensional model of the position and orientation of the prosthesis in the installation position.

2. The device for use in placing a prosthesis in a patient during joint replacement surgery of claim 1, wherein:

the prosthesis alignment member is configured to mate with and engage a rim of the prosthesis in the installation position.

3. The device for use in placing a prosthesis in a patient during joint replacement surgery of claim 1, wherein:
the prosthesis alignment member is configured to mate with an inner surface of the prosthesis in the installation position.

4. The device for use in placing a prosthesis in a patient during joint replacement surgery of claim 1, wherein:
the prosthesis alignment member is configured to mate with an arc of a rim of the prosthesis in the installation position.

5. The device for use in placing a prosthesis in a patient during joint replacement surgery of claim 1, wherein:
the prosthesis alignment member is configured to mate with a circumference of a rim of the prosthesis in the installation position.

6. The device for use in placing a prosthesis in a patient during joint replacement surgery of claim 1, wherein:
the prosthesis alignment member is one of a plurality of prosthesis alignment members extending from the inner surface of the body and configured to mate with the prosthesis in the installation position.

7. The device for use in placing a prosthesis in a patient during joint replacement surgery of claim 6, wherein:
one or more of the plurality of alignment members is configured to mate with a working surface of the prosthesis in the installation position.

8. The device for use in placing a prosthesis in a patient during joint replacement surgery of claim 6, wherein:
one or more of the plurality of alignment members is configured to mate with a rim of the prosthesis in the installation position.

9. The device for use in placing a prosthesis in a patient during joint replacement surgery of claim 1, wherein:
the anatomic alignment member extends around the outer surface of the body.

* * * * *